United States Patent
Grubisic (10) Patent No.: US 6,816,241 B2
(45) Date of Patent: Nov. 9, 2004

(54) LED LIGHT SOURCE-BASED INSTRUMENT FOR NON-INVASIVE BLOOD ANALYTE DETERMINATION

(75) Inventor: Dragan Grubisic, Phoenix, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 214 days.

(21) Appl. No.: 09/956,747

(22) Filed: Sep. 17, 2001

(65) Prior Publication Data

US 2002/0041166 A1 Apr. 11, 2002

Related U.S. Application Data

(60) Provisional application No. 60/235,372, filed on Sep. 26, 2000.

(51) Int. Cl.[7] .......................... G01N 33/48; B60Q 1/12; B60Q 1/24
(52) U.S. Cl. .......................... 356/39; 362/231; 362/241
(58) Field of Search .......................... 356/39, 40, 41; 362/551, 552, 554, 555, 572, 574, 800, 802, 230, 231, 241, 247

(56) References Cited

U.S. PATENT DOCUMENTS

| | | | | |
|---|---|---|---|---|
| 5,313,941 A | * | 5/1994 | Braig et al. | 600/322 |
| 5,348,002 A | * | 9/1994 | Caro | 600/310 |
| 5,348,003 A | * | 9/1994 | Caro | 600/310 |
| 5,424,545 A | * | 6/1995 | Block et al. | 250/343 |
| 5,515,847 A | * | 5/1996 | Braig et al. | 600/316 |
| 5,601,079 A | * | 2/1997 | Wong et al. | 600/322 |
| 5,638,816 A | * | 6/1997 | Kiani-Azarbayjany et al. | 600/316 |
| 5,785,658 A | * | 7/1998 | Benaron et al. | 600/473 |

* cited by examiner

Primary Examiner—Frank G. Font
Assistant Examiner—Roy M. Punnoose
(74) Attorney, Agent, or Firm—Glenn Patent Group; Michael A. Glenn (57) ABSTRACT

A compact, lightweight instrument for non-invasive blood analyte determination employs a light source incorporating an assembly of LED's interconnected within a thermally stable substrate. A large diameter mixer couples the signal to a fiber optic probe for delivering the signal to a tissue measurement site. Back-diffused light is collected and dispersed across an array of photo detectors in a miniature spectrometer instrument. A high-speed DSP executes an algorithm for predicting concentration of a target analyte, which is output to a LCD display. Instrument control is by means of keypad or voice recognition.

High conversion efficiency of the light source results in extremely low power dissipation and virtually no heat generation, making incorporation of the light source and the spectrometer into a single unit practicable. High-speed pulsing of the signal allows application of high-sensitivity, synchronous detection techniques. Speed and flexibility in sequencing LED's allows simultaneous measurement and skin temperature control.

53 Claims, 10 Drawing Sheets

LED LIGHT SOURCE-BASED INSTRUMENT FOR NON-INVASIVE BLOOD ANALYTE DETERMINATION

This application claims the benifit of Provisional Application No. 60/235,372, filed Sep. 26, 2000.

BACKGROUND OF THE INVENTION

1. Field of the Invention

The current invention relates to the field of non-invasive blood analyte measurement. More particularly, the current invention relates to a compact instrument for non-invasive blood analyte determination that employs light emitting diodes (LED's) supported on a thermally stable substrate as a source of light energy.

2. Description of Related Art

Conventional methods of clinical testing have required the use of invasive procedures, such as biopsy and phlebotomy, to sample blood and tissue. Subsequently, the samples were transported to a central location, such as a laboratory, for examination and analysis. There is an increasing trend, however, toward point-of care testing, and even in-home testing. A benefit of this trend is to minimize the turnaround time from when a sample is taken to being able to take action based on test results. At the same time, sampling procedures are becoming less and less invasive. Since they minimize or eliminate the need to handle blood and tissue specimens, minimally invasive and non-invasive procedures drastically reduce biohazard risk, both to the subject and to the practitioner.

The goal of non-invasive blood analyte measurement is to determine the concentration of targeted blood analytes without penetrating the skin. Near infrared (NIR) diffuse reflectance spectroscopy is a promising technology for noninvasive blood analyte measurement and involves the illumination of a spot on the body with low energy near-infrared light (750–2500 nm). The light is partially absorbed and scattered, according to its interaction with chemical components within the tissue, prior to being reflected back to a detector. The detected light is used to create a graph of $-\log R/R_s$, where R is the reflectance spectrum of the skin and $R_s$ is the reflectance of an instrument standard. In infrared spectroscopy, this graph is analogous to an absorbance spectrum containing quantitative information that is based on the known interaction of the incident light with components of the body.

Portable and handheld noninvasive blood glucose analyzers are being developed for point of care and in home use. The development of such devices has been hindered, in part, by the type of light source commonly used in spectrometer instruments. The conventional halogen tungsten lamp found in most spectrometer instruments is large and energy inefficient. It has a high power requirement, thus shortening battery life, generates excessive amounts of heat, requires a long time to stabilize and has a short life expectancy.

Furthermore, conventionally, light emitted from a light source is coupled into an optical probe, or otherwise directed toward a measurement site using space optics consisting of sets of mirrors and lenses. Such arrangements have high space requirements and they are highly vulnerable to mechanical shock.

The prior art provides a few examples of light source assemblies for non-invasive optical sampling. For example, F. Levinson, Light mixing device with fiber optic output, U.S. Pat. No. 5,271,279 (Dec. 14, 1993) describes a light-mixing device for a spectroscopic instrument in which a mixing rod couples light from a light source composed of LED's, die bonded into an electric header, with a plurality of optical fibers. The LED's have differing central wavelengths of emitted light and the mixing rod efficiently mixes the output of the several LED's into a single beam of light and then splits the beam in uniform fashion across the several optical fibers. The described device does not provide any means of collecting light energy emitted from a sample. It also doesn't provide any means of shaping light as it is emitted from the individual LED's. While the header of the LED assembly acts as a conduit for excess thermal energy produced by the LED's, it would be desirable to provide an active cooling element to provide an environment that maximizes energy efficiency of the LED's.

R. Rosenthal, Light probe for a near infrared body chemistry measurement instrument, U.S. Pat. No. 6,134,458 (Dec. 31, 1991) describes a light probe for a spectroscopic instrument that includes an illumination ring having external facets. LED's positioned about the facets emit light into the illumination ring; light is coupled to the measurement site by bringing the body part bearing the site into contact with the illumination ring. An optical detector is located coaxially with the illumination ring. While the Rosenthal device does provide a means of collecting light energy emitted from the site, it doesn't provide any means of mixing the light energy emitted from the several LED's. The light from the LED's is coupled directly with the probe, without the interposition of a mixer to thoroughly blend the wavelength content of the light. The Rosenthal device also does not provide any means of shaping the light beams emitted from the LED's, nor does it provide a thermally stable substrate for the LED's. Furthermore, no active cooling system is provided to optimize operating temperature of the LED's.

Spectrometer instruments for measuring concentration of blood analystes such as glucose are known. Typically, such devices are not intended to be portable. For example, K. Kaffka, L. Gyarmati, I. Vályi-Nagy, I. Gödölle, G. Domján, J. Jáko, Method and apparatus for rapid non-invasive determination of blood composition parameters, U.S. Pat. No. 5,947,337 (Oct. 26, 1999) describe an instrument for non-invasive glucose measurement. The described instrument irradiates the distal phalanx of a subject's finger with light in the near IR. The transmitted or reflected radiation is detected and analyzed and an estimate of blood glucose level made. There is no indication that the device described by Kaffka, et aL is portable or handheld. The signal is coupled with a fiber optic probe by means of a conventional arrangement of lenses and mirrors. The space requirements of such an arrangement are unsuited to a handheld device. Illumination fibers and collection fibers are provided in separate structures, also requiring excessive amounts of space.

M. Block, L. Sodickson, Non-invasive, non-spectrophotometric infrared measurement of blood analyte concentrations, U.S. Pat. No. 5,424,545 (Jun. 13, 1995) describe an instrument for noninvasive blood analyte determination that relies on calorimetric analysis to arrive at a blood analyte determination. The described device is not handheld or portable. As with the previous reference, a light beam is coupled with an illumination fiber by means of lenses and mirrors, with similar disadvantages.

T. Aldrich, Non-invasive blood component analyzer, U.S. Pat. No. 6,064,898 (May 16, 2000) describe a non-invasive blood component analyzer that also provides built-in path length monitoring to allow use in subjects of varying finger size. The Aldrich device is not a handheld or otherwise portable device. It provides a light source either from LED's or from a lamp. No structure is provided for coupling the light beam from the light source; the light is simply emitted in the vicinity of the sampling site and coupled through the atmosphere. The current device, plus all of the previously described devices for blood analyte determination, while they often employ several LED's as a light source, do not provide the LED's in structured arrays; and they do not provide substrates to lend the LED's mechanical support, thermal stability and electrical connectivity.

Handheld spectrometers are known in the prior art. K. Levin, S. Kerem, V. Madorsky, Handheld infrared spectrometer, U.S. Pat. No. 6,031,233 (Feb. 29, 2000) describe a handheld infrared spectrometer. Space is conserved by aligning the optics and eliminating fibers. Light is emitted from a conventional lamp and passed through an acousto-optical tuning filter (AOTF) for wavelength selection. The filtered light is focused through one or more lenses and directed toward the measurement site through a window. While the design is highly spaceefficient, allowing for a truly handheld spectrometer, the use of an AOTF for wavelength selection requires a wavelength synthesizer and an RF amplifier. Furthermore, a conventional lamp for a light source is energy inefficient, shortening battery life and generating excessive amounts of thermal energy.

H. Van Aken, A. Kravetz, K. Garde, W. Weber, J. Corrado, Handheld portable spectrometer, U.S. Pat. No. 5,319,437 (Jun. 7, 1994) describe a handheld spectrometer. The Van Aken device employs a conventional lamp, with all of its attendant disadvantages.

An example of a portable noninvasive blood glucose analyzer is provided by R. Rosenthal, Instrument for non-invasive measurement of blood glucose, U.S. Pat. No. 5,077,476 (Oct. 17, 2000). Rosenthal describes a hand-held instrument for non-invasive measurement of glucose. One or more LED's are used to provide a point source of near IR energy of a predetermined bandwidth. The emitted energy is coupled with the sampling site by means of a focusing lens. The Rosenthal instrument does not provide a wide band signal from an array of LED's emitting in overlapping wavelength regions. The space requirements for the mirror arrangement and the detector arrangement are such that the overall size of the instrument would be unwieldy for a handheld device. The Rosenthal device does not provide a spectrum analyzer or a linear detector array.

There exists, therefore, a need in the art for a long-lived, space efficient, energyefficient light source assembly for non-invasive optical sampling. It would be desirable to provide a light source assembly that employs light-emitting diodes (LED's) as a light source. Furthermore, it would be desirable to combine the LED's into a compact sub-assembly by attaching LED's to a substrate that provided electrical connections, and mechanical and thermal stability. It would be a great advantage to provide a simple space-efficient means of coupling light from the light source with an optical probe that is resistant to mechanical shock and perturbation, while mixing wavelengths thoroughly and normalizing light intensity. It would be a further advantage to provide a means of optimizing the operating temperature to maximize LED efficiency. It would be a significant technological advance to incorporate such a light source assembly into a lightweight, compact instrument for non-invasive blood analyte determination.

SUMMARY OF THE INVENTION

In a first embodiment, the invention provides a LED-based light source assembly for non-invasive optical sampling. A wide band signal is achieved by combining LED's, singly or in groups, that emit in overlapping wavelength bands. LED's are combined into a LED/substrate sub-assembly, in which LED's, attached to reflectors mounted in a thermally stable substrate, are electrically connected by means of bonding wires. A LED light source assembly includes the LED/substrate sub-assembly; a mixer, consisting of a large diameter fiber optic having a hollow center to couple the signal to a probe; a collection fiber, threaded through the hollow center, for collecting light emitted from the sample under test; a printed circuit board, in which the LED/substrate sub-assembly is seated, and having electrical contacts for connecting the LED's to an LED driver; and a cooling system for stabilizing the substrate temperature.

In a second embodiment, the invention provides a compact, lightweight instrument for non-invasive blood analyte determination that incorporates the light source assembly provided by the first embodiment. The instrument includes the LED-based light source assembly; an optical module that includes a miniature spectrum analyzer having a grating to focus and disperse the light received from the collection fiber and a linear detector array for receiving the dispersed spectrum; an LED driver; a digital electronics module for processing the spectrum and estimating concentration of a target analyte; and a display, for outputting the target analyte concentration.

The high conversion efficiency of the light source results in extremely low power dissipation and virtually no heat generation, making incorporation of the light source and the spectrometer into a single unit practicable. High-speed pulsing of the signal allows application of high-sensitivity, synchronous detection techniques. Speed and flexibility in sequencing LED's allows simultaneous measurement and skin temperature control.

DETAILED DESCRIPTION

Spectrometer instruments have conventionally employed a light source consisting of a halogen-tungsten lamp. For portable and handheld applications, such light sources have several disadvantages: most notably that they are neither space nor energy efficient. In addition, these light sources generate excessive amounts of heat, take a long time to stabilize and have a short life expectancy.

In a first embodiment, the invention provides a light source assembly for noninvasive optical sampling that employs light emitting diodes (LED) as the light source. An LED-based light source offers a number of advantages. Among them are:

Compact Size;

LED's can be selected and combined to emit light only in a spectral region of interest;

High light conversion efficiency/low heat generation;

Light intensity is easily modulated;

Provides the option of continuous wave and pulsed modes of operation; and

Long Lifetime (>100,000 hrs.).

Recent applications using superluminescence light emitting diodes (LED) as a replacement for incandescent lighting, as well as for billboards, show that LED's are well suited as light sources in spectrometry applications. While these applications have employed superluminescence LED's that emit in the visible wavelength region, it is apparent that future improvements offer even more promise regarding the light levels available from such light sources

Light-Emitting Diodes (LED)

LED's are solid-state components that emit a narrow wavelength band of peak intensity and spectral width, determined by construction. Construction may vary depending on performance requirements: single-junction, hetero-junction or super-luminescence. Also, chip size is highly variable, ranging from about 0.1×0.1×0.1 mm to about 1×1×0.1 mm. The wavelength band is determined by the material used to build the LED, thus it is not a consequence of the physical construction of the LED.

Figure 1:
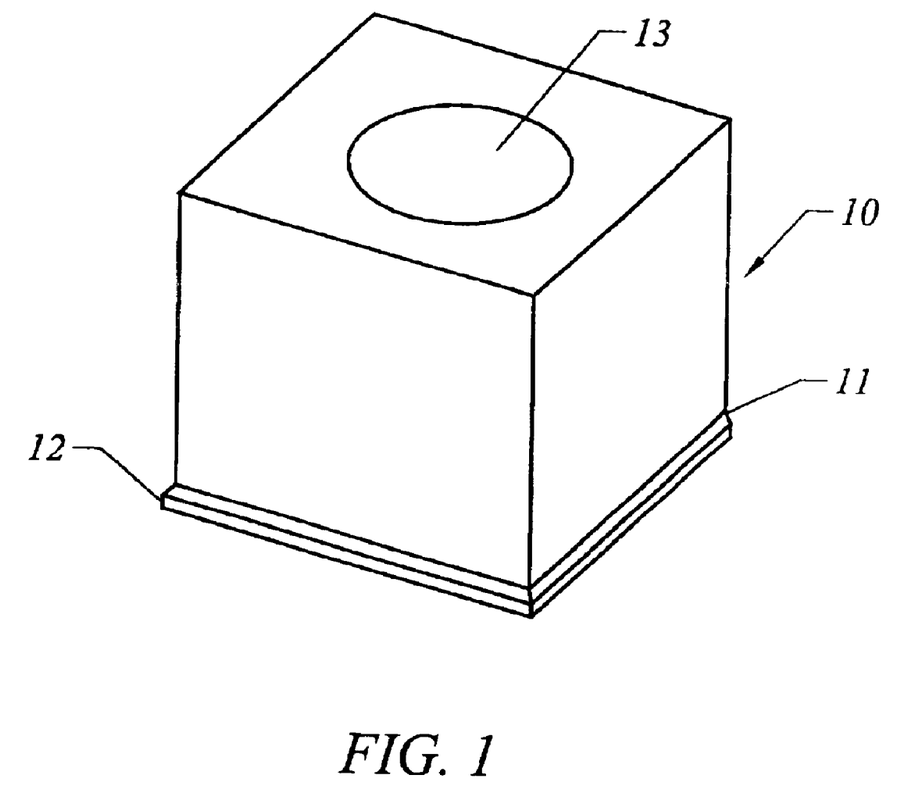
FIG. 1 shows a typical light emitting diode (LED) in an upside down configuration, wherein the LED has a light emitting junction at the bottom of the chip and light is emitted through the top of the chip.

Since LED's emit a narrow wavelength band, to obtain a wide band light source, a combination of different LED's must be used. In the present embodiment of the invention, individual LED types that emit in different wavelength bands with overlaps at full-width half maximum (FWHM) spectral points or better are selected and combined in a single sub-assembly to provide a wide band light source. Furthermore, since individual LED's can be so small (i.e. 300×300×200 microns), the invented light source assembly is extremely compact, while generating very little heat due to high conversion efficiency. Referring now to FIG. 1, a typical LED 10, in an upside down configuration, is shown. A light-emitting junction 11 produces light from an applied voltage. Back metallization 12 along the bottom reflects the generated light, greatly improving energy efficiency. A top contact 13 together with the back metallization enables electrical connections to and from the LED.

LED Substrate

As mentioned before, it is necessary to combine several different types of LED's in order to build a wide band light source. A novel substrate provides a housing and electrical interconnections for the selection of LED's that make up the light source. The substrate provides several features essential to the proper function of the invented light source assembly:

Mechanical support and compactness;

Electrical connections;

Light beam shaping;

Light intensity profile shaping; and

Thermal stability.

Furthermore, the invented LED substrate advantageously provides a high degree of flexibility with respect to the interconnection of the LED's; for example, by allowing individual access to selected LED's, or grouping LED's by type to improve the power level to the selected type, or to intentionally increase the light power level at selected wavelength ranges of interest. By virtue of the flexibility of the LED substrate desing, other embodiments of the invention are possible in which other light sources are provided, in addition to the LED's, such as laser diodes, and/or sensors for monitoring and controlling conditions at the measurement site, such as skin temperature or surface hydration.

Figure 2A:
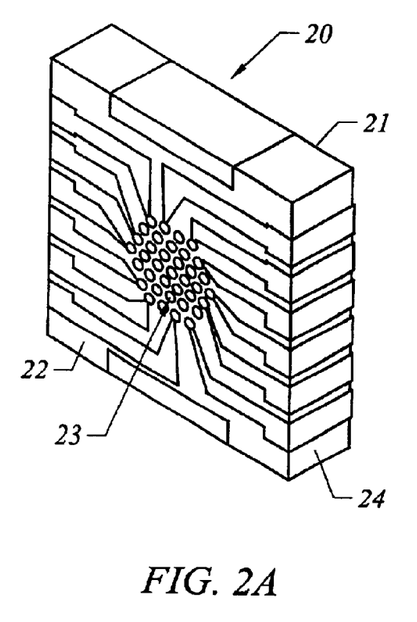
FIGS. 2a and 2b show top and bottom views, respectively, of a substrate for LED's according to the invention.
Figure 2B:
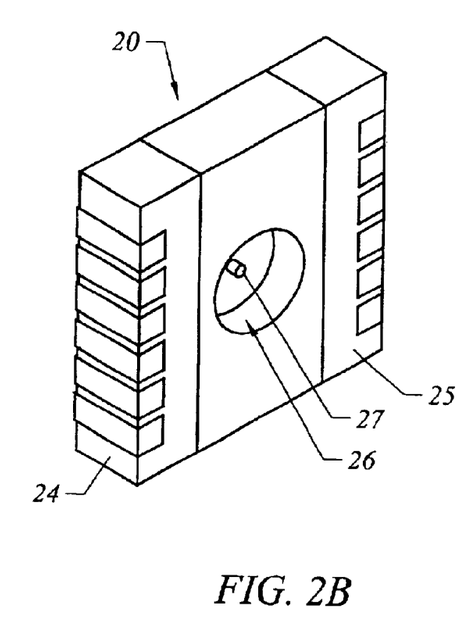
Figure 3:
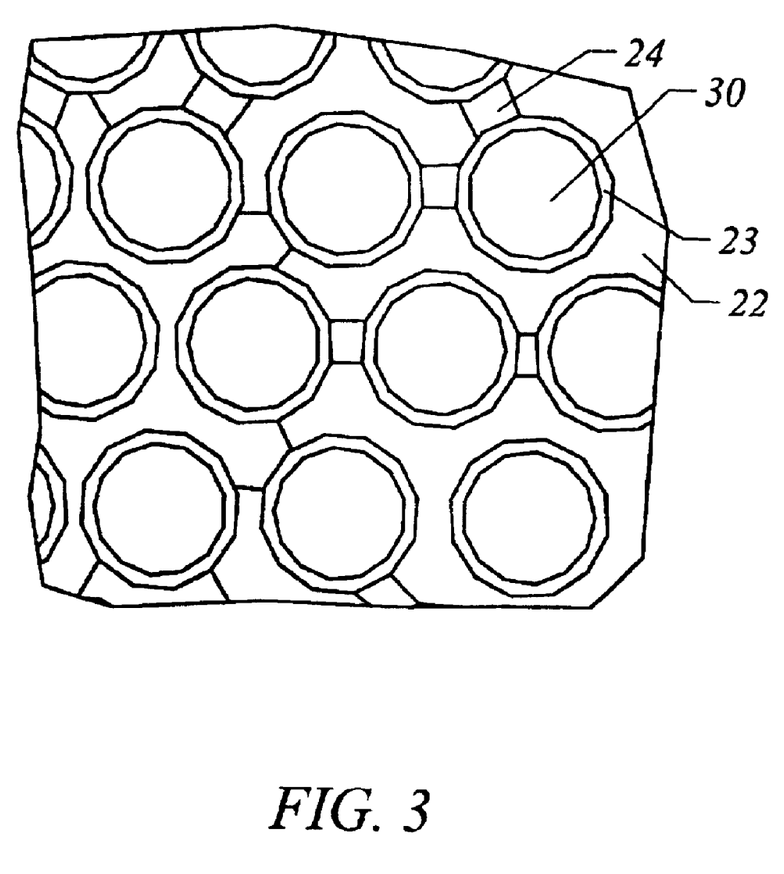
FIG. 3 provides a detailed view of the substrate of FIG. 2, showing parabolic reflectors in which LED's are to be mounted, according to the invention.

Referring now to FIG. 2a, the invented LED substrate 20 according to the invention is shown. The main body 21 of the substrate may be fabricated from any material that has sufficient mechanical strength, good thermal conductivity and that can be easily shaped into the required geometry. Examples of such materials are different types of ceramics and plastic resins. On the anterior face 22 of the substrate 20, an array of wells 23 is provided into which the LED's are mounted. A metallization pattern 24 on the sides and both faces of the substrate provides electrical contacts for electrically connecting the LED's to an LED driver, described in greater detail below. Viewing the posterior face 25 of the substrate, as shown in FIG. 2b, a large well 26 receives a thermoelectric cooler, described in detail below. A conduit 27 communicates with the anterior face to provide passage for a collection fiber, also described below. FIG. 3 shows a detailed view of the anterior face 22 of the substrate body 21. Each well 23 provides a parabolic reflector 30 within which the LED's 10 are to be mounted. Since the light emitted from the LED's 10 is Lambertian in nature and emanates from the junction area 11 on the sides as well as the top surface, the reflectors 30 are necessary to from a low divergence light beam from each LED 10. A well-behaved light beam improves light coupling efficiency, whether the light beam is coupled into a fiber or directly to a sample under test. FIG. 3 also provides a detailed view of the metallization pattern 24. The metallization pattern can be designed to either allow electrical connections to every LED 10 singly, or LED's can be interconnected into groups, offering the advantage of built in redundancy. Subsequently, the single LED's, or the groups are connected to the LED driver. The electrical connection scheme within the groups, as well as the overall design of the connection scheme varies according to application and overall instrument design. The LED substrate is fabricated using conventional methods.

LED/Substrate Subassembly

Figure 4:
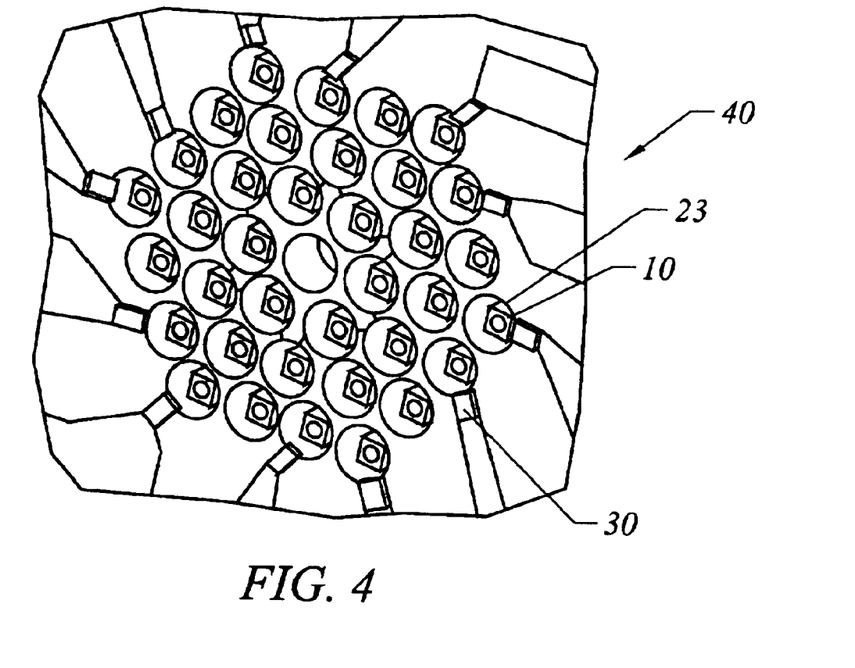
FIG. 4 provides a close-up, detailed view of a substrate/LED subassembly, according to the invention.
Figure 5:
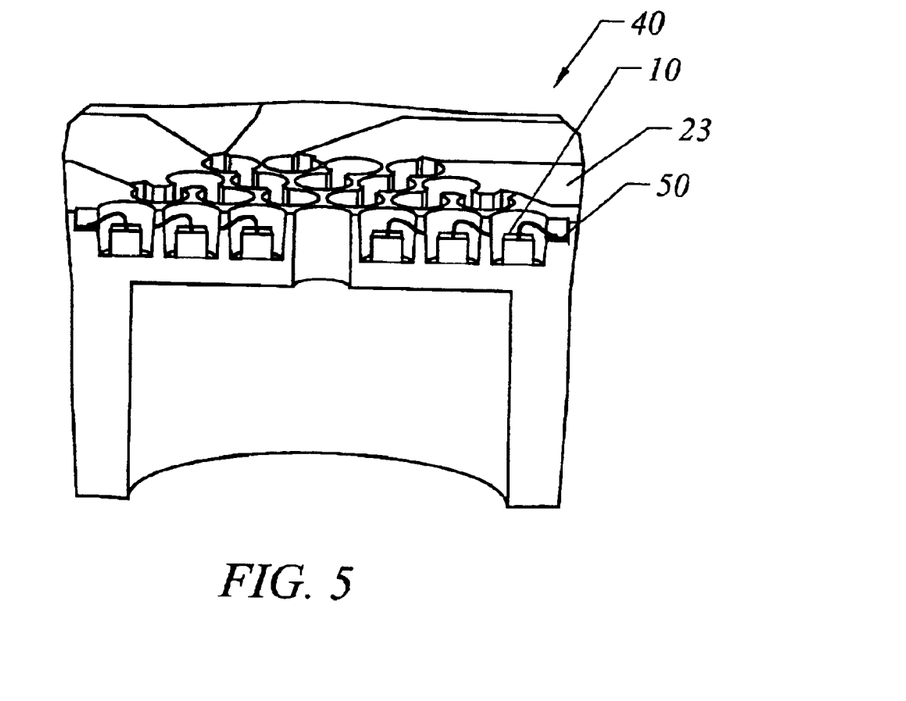
FIG. 5 provides a section view of the subassembly of FIG. 4, according to the invention.

As FIGS. 4 and 5 show, the LED's and the substrate are fabricated into a subassembly 40. Each LED 10 is centered within its respective well 23 and fastened to the bottom of the reflector 30, preferably with electrically conductive epoxy. As shown in FIG. 5, individual LED's 10 are bonded and electrically interconnected using bonding wires 50 of appropriate size. Preferably, the bonding wires 50 are gold; the size of the wire is dictated by the current drive requirement of the corresponding LED and the diameter of the top contact 13. The anterior face of the entire assembly, bearing the mounted and electrically interconnected LED's is covered with an appropriate optical epoxy or polymeric resin material (not shown) having favorable transmission characteristics in the spectral range represented by the light emitting LED's of the light source assembly 60. This material provides two important functions:

Mechanical protection for fragile bond wires; and

Matching refreactive index of substrate medium, minimizing Fresnel's losses.

The filling material preferably has a refractive index approximately equal to:

$$\sqrt{n_{LED} * n_0}$$

where:

$n_{LED}$=Light emitting diode index of refraction; and $n_0$=Surrounding medium index of refraction.

LED Light Source Assembly

Figure 6:
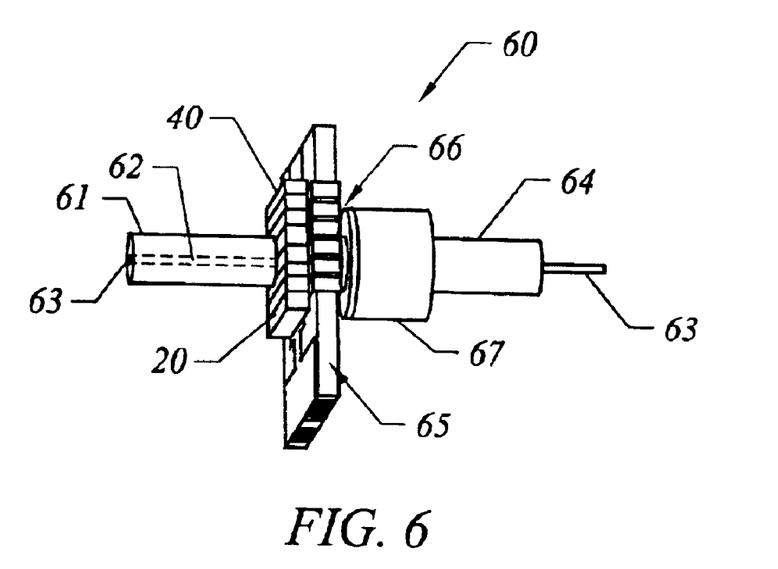
FIG. 6 provides a three dimensional rendering of a LED light source assembly according to the invention.

Referring now to FIG. 6, shown is the LED/substrate assembly integrated into a light source assembly 60. Emitted light must be coupled to a sample interface, or otherwise directed toward the measurement site. Conventionally, space optics, consisting of arrangements of mirrors and lenses are used for this purpose. However, the space requirements of these arrangements render them unsuitable for compact, space efficient applications. Furthermore, conventional optical arrangements are highly sensitive to mechanical shock and other perturbations, rendering them unsuitable for use in handheld devices. The invention utilizes an optical mixer 61, enjoying the advantages of simplicity and compactness, for this purpose. Preferably, the mixer 61 is a special, large diameter fiber, in which the size is determined by the optimal pathlength of the light through the skin, and having a hollow center 62 to accommodate a collection fiber 63. The preferred material for the mixer 61 is low $^-$OH silica fiber, however other materials having a high refractive index, such as sapphire or silicon, would also be suitable. The mixer provides a medium for thorough mixing of wavelength content and normalization of light intensity in the light beam emanating from the LED's without introducing an unacceptable level of light loss. Preferably, the mixer 61 is mounted onto the substrate 20 at the same time it is encapsulated with resin, however the mixer may also be mounted by means of a mechanical fixture.

Preferably, the collection fiber 63 is a low $^-$OH silica fiber having a core diameter of approximately 600 microns. As shown, the collection fiber is a short, straight piece of fiber, fixedly positioned in the hollow center 62 of the mixer, such that it passes through all the components of the light source assembly, in order to increase light collection efficiency. The collection fiber 63 may be held stationary by gluing it into position within the mixer 61. The end of the collection fiber is reinforced with a ferule 64 that is dimensioned to fit the entrance of the spectrum analyzer, described below.

Figure 7:
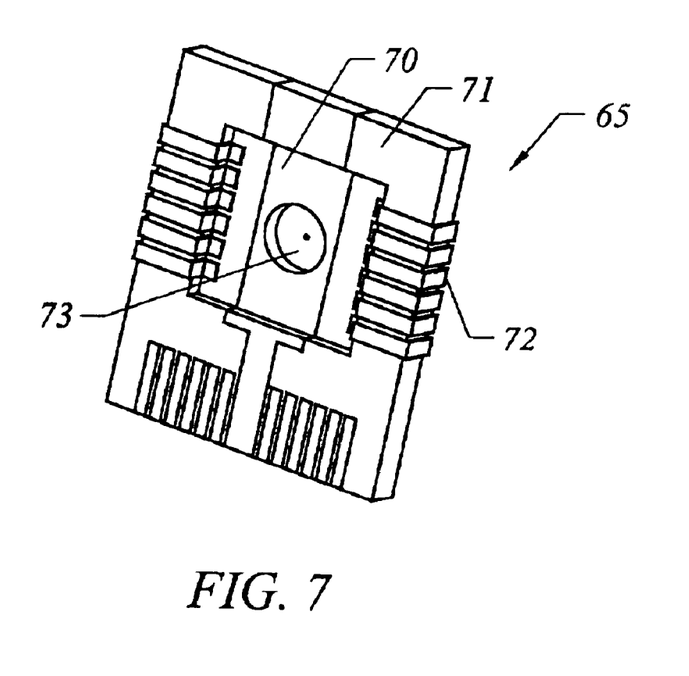
FIG. 7 provides a three dimensional rendering of a LED light source assembly printed circuit board (PCB) according to the invention.

As FIG. 6 shows, the subassembly consisting of LED's 10, substrate 20, mixer 61 and collection fiber 63 is mounted into a self-aligning indent 70 on the anterior face 71 of a printed circuit board (PCB) 65, shown in detail in FIG. 7, that functions to facilitate electrical connections 72 between driving electronics and the rest of the light source while providing the substrate 20 additional mechanical support.

The self-aligning feature is provided by an aperture 73 that penetrates the PCB 65 from the floor of the indent 70 to the posterior face of the PCB, allowing placement of a thermoelectric cooler 66, the cold side of which fits into the well 26 on the posterior face 25 of the substrate 20. While the primary function of the thermo-electric cooler 66 is to stabilize the substrate temperature, it also provides a moderate cooling effect, since LED efficiency is dramatically improved at lower temperatures. A proportional heat sink 67 is attached to the "hot" side of thermo-electric cooler 66 for power efficient operation.

Due to its energy and space efficiency, the invented LED based light source assembly 60 is ideally suited for use in a portable instrument for non-invasive measurement of blood analytes such as glucose. A compact, lightweight instrument for non-invasive blood analyte determination incorporating the light source assembly 60 is described below.

Instrument for Non-invasive Blood Analyte Determination

Figure 11:
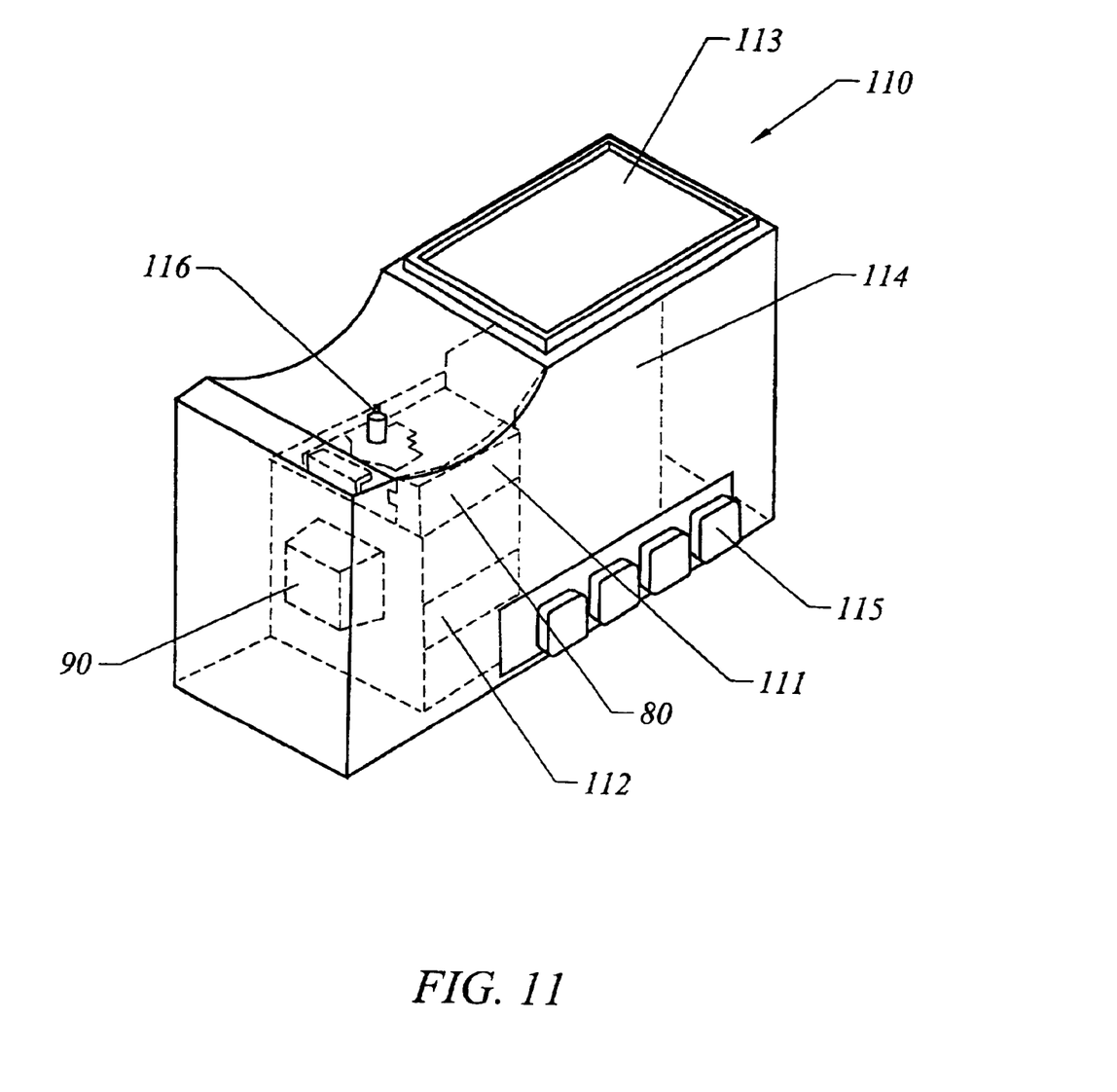
FIG. 11 provides a three dimensional rendering of a LED light source-based instrument for non-invasive blood glucose measurement, according to the invention.

In overview, the instrument 110, shown in FIG. 11, irradiates a sampling site on the skin of a subject with a beam of wideband light. The back-diffused light, transmitted or reflected by the skin, is collected. Spectral content is analyzed by dispersing the light beam against a grating within a spectrum analyzer. The dispersed spectrum is projected across a linear detector array sensitive in the wavelength range of interest. The detector array records the received signal and converts it to a voltage. After the signal is conditioned and digitized, a signal processor within a digital electronics module analyzes the signal according to a prediction algorithm to estimate blood level of the target analyte.

I. Optical Module

Figure 10:
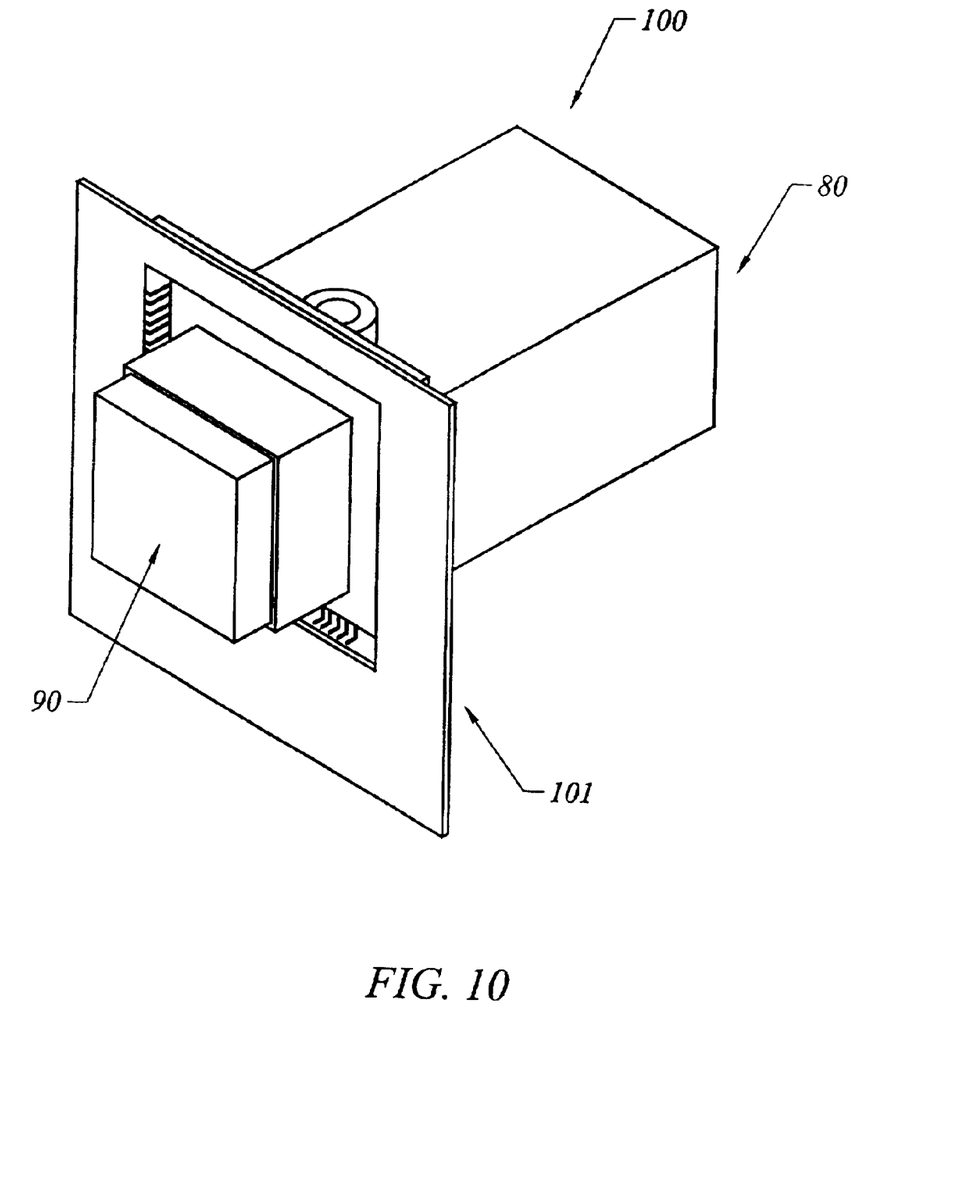
FIG. 10 provides a three-dimensional rendering of an optical module including the miniature spectrometer of FIG. 8 and the PDA module of FIG. 9, according to the invention.

As shown in FIG. 10, the optical module 100 includes a miniature spectrum analyzer 80 and an associated linear detector array module 90.

Spectrum Analyzer

Figure 8:
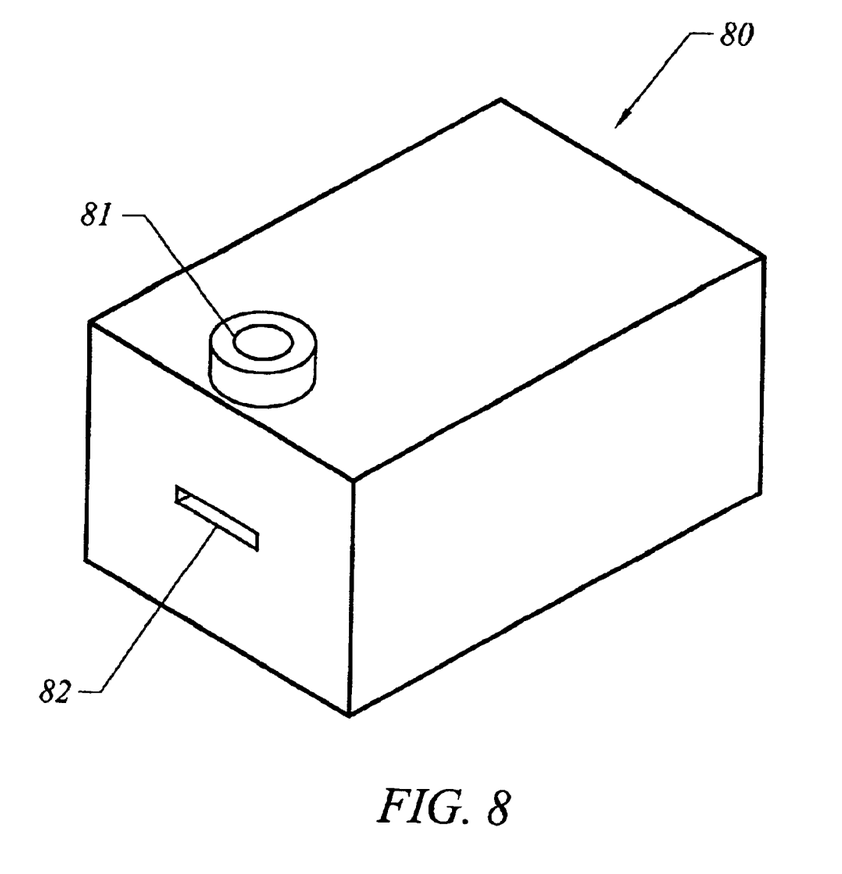
FIG. 8 provides an isometric view of a miniature spectrum analyzer, according to the invention.

As FIG. 11 shows, the invented instrument 110 for non-invasive blood analyte determination incorporates a spectrum analyzer 80, wherein a signal is received from the collection fiber 63, and dispersed against a holographic grating (not shown). As FIG. 8 shows, the spectrum analyzer has an input slit 81 and an output slit 82. In order to deliver a light beam to the detector array having a width equal to, or about equal to, the length of the detector array, the width of the input slit 81 duplicates that of an individual pixel of the detector array. The height of the array (i.e. 500 µm) dictates the size of the collection fiber (i.e. 600 µm). A light beam is emitted from the collection fiber 63 and received by the input slit of the spectrum analyzer 81. The spectrum analyzer further includes an angled mirror (not shown) and a concave holographic grating (not shown) in a conventional arrangement, well known to those skilled in the art. The mirror, at an angle of 45°, folds the light beam received from the collection fiber 63 and directs it toward the diffraction grating. The diffraction grating both disperses the light beam into spectral components and focuses it at the focal plane of the detector array. The output slit 82 of the spectrum analyzer is dimensioned to be slightly wider than the detector array in order to avoid clipping the dispersed spectrum as it is emitted toward the detector array through the output slit. A flat field region of the dispersed spectrum is created through the front slit at the plane where the surface of the linear detector array is positioned, in which the area of the flat field region is approximately equal to the total active area of the detector array. It should be noted that, while the described spectrum analyzer is preferred, other configurations may also be suitable, as long as they meet the functional requirements of small size and low stray light emission imposed by the instrument's use as a blood glucose analyzer, characteristics that are critical in the design of a hand-held instrument.

Linear Detector Array Module

Figure 9:
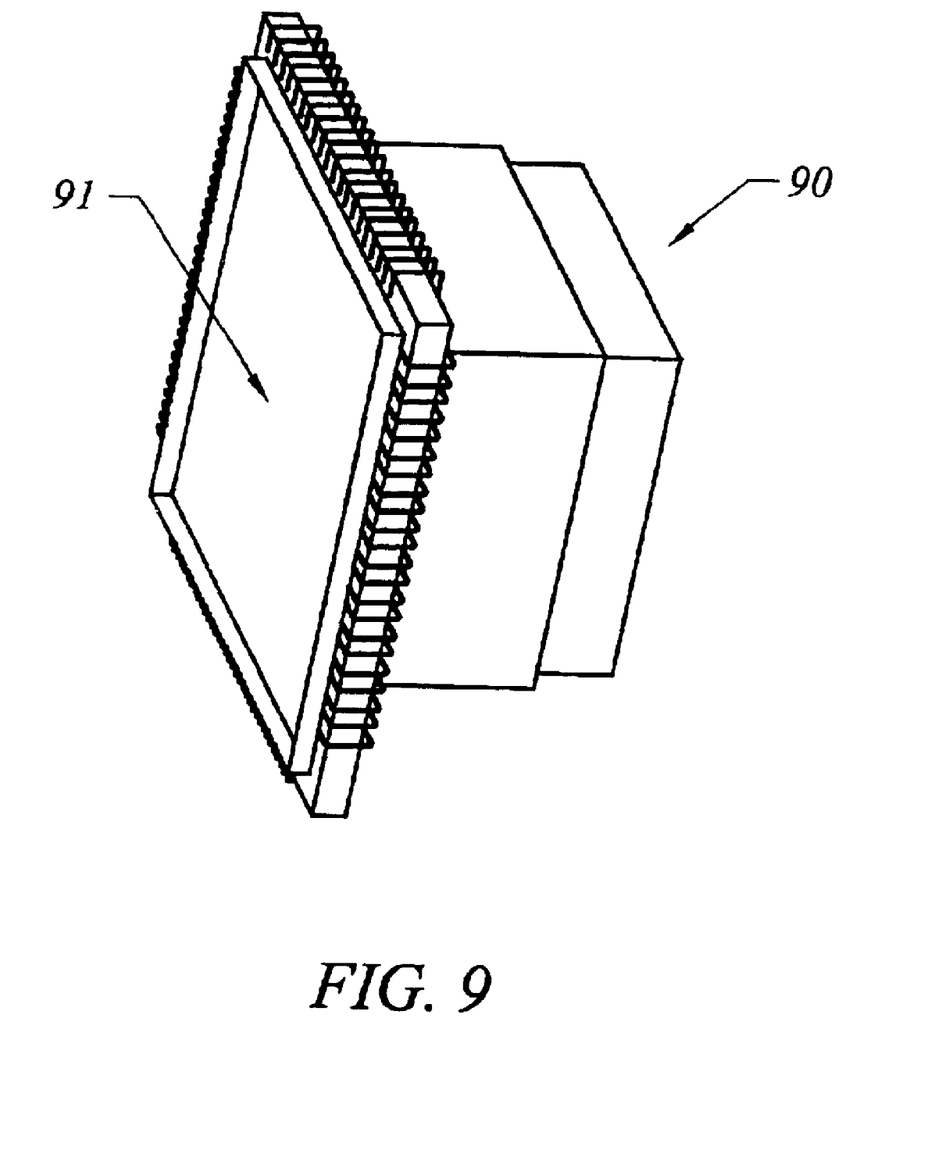
FIG. 9 provides a three dimensional rendering of a photo diode array (PDA) module, according to the invention.
Figure 12:
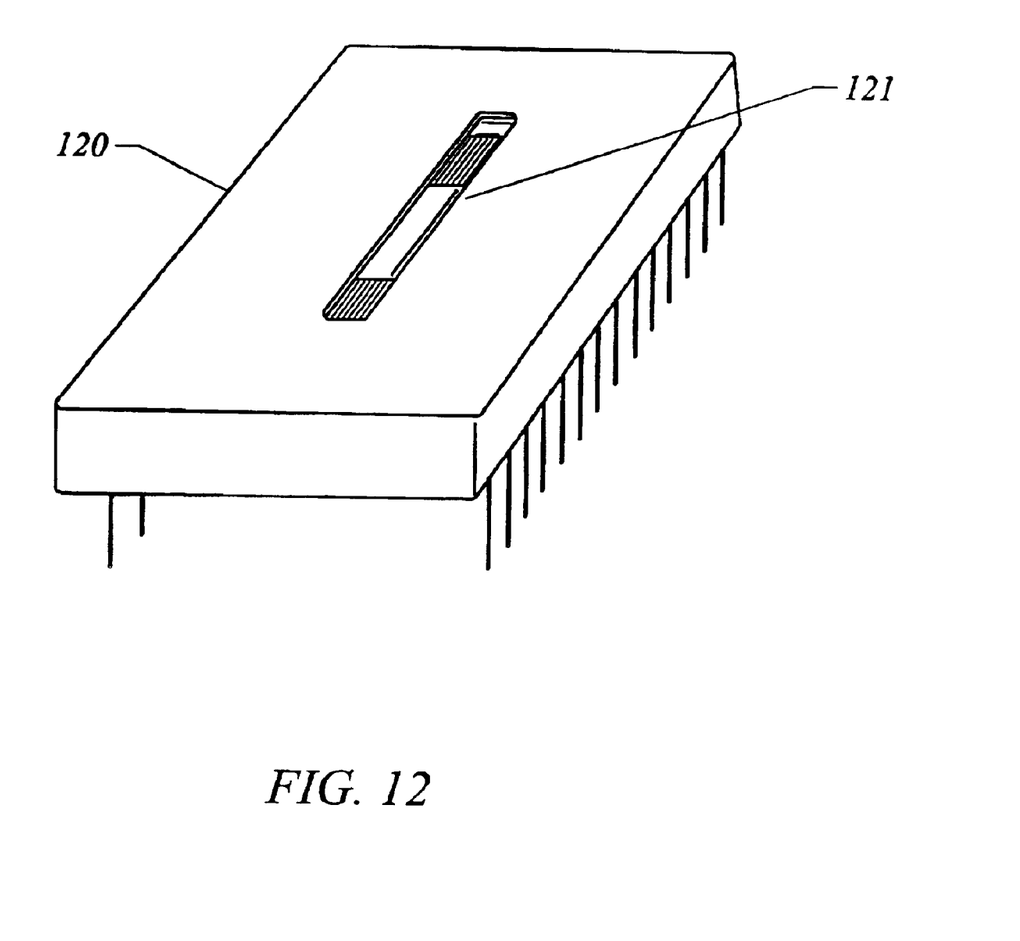
FIG. 12 shows an alternate version of a PDA module, according to the invention.

A linear photo diode array (PDA), in which each photodiode is optimized for the wavelength range of interest, records the whole spectrum. FIG. 9 shows an example of a PDA module 90. The PDA module 90 incorporates the detector in a conventional manner apparent to those skilled in the art of integrated circuit design and electronics packaging. As previously mentioned, the module 90 is positioned in such a way that a flat field image of the dispersed spectrum is projected toward the hybrid focal plane located behind the face 91 of the detector array module. FIG. 12 provides an alternate version of a PDA module 120 that includes a linear array of photodiodes 121. Such linear arrays are commonly known in the art as focal plane arrays. The hybrid focal plane consists of a linear array of photodiodes and silicon multiplexer chips that are interconnected through wire-bonding and substrate metallization. The photodiodes are manufactured from a material system suited to the wavelength range of interest, for example, InGaAs, Ge, or InAs. The linear photodiode array records signals by detecting light and converting the light to a signal, the voltage of which is representative of the intensity of the detected light. Each individual photodiode, representing a single pixel, simultaneously records a one-pixel portion of the projected spectrum, so that the entire spectrum is recorded. The signals are then read out through the silicon multiplexer chips. Subsequently, measured values are then clocked serially out through signal conditioning and Analog-to-Digital circuitry, described in greater detail, below. Preferably, the multiplexer chips have the following characteristics:

Low system noise;

Programmable gain;

Offset voltage cancellation; and

High readout speed.

Optimum acquisition speed in scans per second is determined by the available light level (integration time) and readout speed. The current embodiment of the invention provides readout speed in a range from approximately 100 scans per second to 1000 scans per second.

The linear detector array module 90 is incorporated into a single PCB 101 with the above-mentioned signal conditioning circuitry and ADC.

Signal conditioning is provided by conventional circuitry performing any of the following:

buffering;

impedance matching;

frequency smoothing; and level-shifting.

Following signal conditioning, the signal is digitized by means of a conventional analog-to-digital converter (ADC).

II. Electronics

LED Driver

As shown in FIG. 11, an LED driver circuit 111 supplies power to and controls illumination of the LED's 10 of the light source assembly 60. Preferably, the LED driver 110 provides the following capabilities:

Addressability of each serially connected group of LED's/ individual LED's, one at a time;

Simultaneous addressability of all groups/individual LED's (LED) in the light source;

Flexible sequencing of any group of/individual LED based on preprogrammed sequences stored in the memory; and Amplitude modulation of light intensity. Additionally, the LED driver circuit sources very short pulses, 100–400 nanoseconds in duration, with programmable high peak current of up to 10 amps. Also, it provides means to drive the LED's in continuous wave mode at moderate current levels of 100–500 mA and the ability to drive the LED's under either AC or DC conditions. LED drivers having the capabilities described are well known to those skilled in the art, therefore a detailed illustration of the LED driver is not shown.

High Speed Digital Electronics Module

A high-speed digital electronics module 112, incorporating a digital signal processor (DSP) provides the signal processing functionality necessary to execute the glucose measurement algorithm, recorded in a non-volatile memory such as ROM (read-only) or EPROM (electronically programmable read-only). Signal processing functionalities include:

High level—performing all necessary sequencing and synchronization of events needed for accurate blood analyte determination; and Low Level—monitoring status of important instrument indicators, acquiring data. Volatile memory (RAM) is provided for storage of digital values.

Measurement status indicators as well as results are displayed on the high resolution LCD 113, further described below.

Power Supply (114)

While various light, high efficiency batteries are suitable as a power supply, the instrument preferably uses a nickel-metal-hydride type battery 114, designed to support instrument power requirements, while being size-and weight-optimized, in order to meet instrument portability requirements.

III. Controls and Display

Control over the instrument is exercised through a panel of push buttons 115. In an alternate embodiment, hands-free control is provided by means of spoken prompts, recognized by a speech recognition chip on the digital module 112. Measurement status indicators, results and reports are displayed on the high resolution LCD screen 113, positioned on the top of the instrument for improved visibility.

The small size and compactness of the instrument 110, shown in FIG. 11, are achieved primarily through the use of the LED light source and the unique scheme employed to illuminate the sample site and collect light from it. The light source is positioned very close to the sample site, at a distance dictated by the mixer length necessary to achieve sufficient spectral and intensity mixing. Light emitted by the LED's 10 is coupled to the sample interface 116 by the mixer 61. In the preferred embodiment of the invention, the sample interface 116 consists of a fiber optic probe that contacts the sample site, usually the skin of a live subject. The design of the light source assembly and the central position of the light collection fiber allow placement of the spectrum analyzer in close proximity to the light source itself. Since virtually no heat is generated by the light source, it is natural that the spectrum analyzer and the light source itself be combined into one module.

Although the invention has been described herein with reference to certain preferred embodiments, one skilled in the art will readily appreciate that other applications may be substituted without departing from the spirit and scope of the present invention. Accordingly, the invention should only be limited by the claims included below.

What is claimed is:

1. A light source assembly for non-invasive optical sampling, comprising:

a plurality of LED's, wherein at least one of said plurality of LED's emits at a wavelength region different from and overlapping with that of at least another of said plurality of LED's;

a LED substrate, said substrate providing mechanical support for said LED's, so that said LED's and said substrate form a LED/substrate subassembly;

means for electrically connecting said LED's;

means for shaping light beams emitted from said LED's;
means for controlling light intensity profile;
means for coupling said signal to a sample interface;
means for collecting light emitted from said sample;
wherein said means for shaping light beams emitted from said LED's comprises a plurality of parabolic reflectors, wherein each reflector is mounted within a well on an anterior face of said substrate, and wherein each of said LED's is fixedly attached within a corresponding reflector, so that divergence between light beams is minimized.

2. The assembly of claim 1, wherein said LED's are any of single junction, hetero-junction and super-luminescence LED's.

3. The assembly of claim 1, wherein combining light beams encompassing said wavelength regions produces a single wide band signal.

4. The assembly of claim 1, wherein said substrate has a posterior face and sides.

5. The assembly of claim 4, wherein said means for coupling said signal to a sample interface comprises a mixer, said mixer comprising a large diameter fiber optic having a hollow center and having a high index of refraction, so that wavelength content and intensity of light beams emanating from said LED/substrate sub-assembly are thoroughly mixed without introducing additional light loss.

6. The assembly of claim 5, wherein said mixer is fabricated from one of low OH⁻ silica, sapphire and silicon.

7. The assembly of claim 5, wherein said mixer is fixedly mounted on said anterior face of said substrate.

8. The assembly of claim 5, wherein said means for collecting light emitted from said sample comprises a collection fiber, said collection fiber comprising a second fiber optic threaded through said hollow center and passing through a conduit from said anterior face of said substrate to a well in said posterior face of said substrate, said well being dimensioned to receive a temperature regulation element.

9. The assembly of claim 8, wherein said collection fiber has a core diameter of approximately 600 microns, and wherein said collection fiber is fabricated from low OH⁻ silica.

10. The assembly of claim 8, wherein said means for electrically connecting said LED's comprises bonding wires for interconnecting said LED's.

11. The assembly of claim 10, where said means for electrically connecting said LED's further comprises a metallization pattern on the anterior face and sides of said substrate, said metallization pattern forming electrical contacts for contacting said bonding wires.

12. The assembly of claim 11, wherein said means for electrically connecting said LED's further comprises a metallization pattern on a printed circuit board (PCB), said PCB having an anterior face and a posterior face, said anterior face of said PCB defining a self-aligning indent adapted to receive said LED/substrate sub-assembly, said metallization providing electrical contacts that contact said electrical contacts on said substrate when said substrate is seated in said indent and that, in turn, contact a LED driver, so that said LED's are electrically connected to said LED driver.

13. The assembly of claim 12, wherein said LED's are connected to a LED driver individually.

14. The assembly of claim 12, wherein said LED's are connected to a LED driver in groups.

15. The assembly of claim 12, wherein said PCB defines an aperture, so that said substrate conduit and said PCB aperture align when said LED/substrate sub-assembly is seated in said PCB.

16. The assembly of claim 15, wherein said means for regulating temperature comprises a thermo-electric cooler, having a cold side and a hot side, that fits through said aperture to be received by said posterior well so that said cold side is in contact with said posterior face of said substrate; and
a heat sink, said heat sink in contact with said hot side of said cooler;
wherein said thermoelectric cooler and said heat sink together comprise a sub-assembly.

17. The assembly of claim 16, further comprising a support ferrule, wherein said collection fiber passes through said PCB aperture and said thermoelectric cooler-heat sink sub-assembly to be received by said ferrule at the posterior face of said PCB.

18. The assembly of claim 1, wherein said LED/substrate sub-assembly is coated with one of optical epoxy and a polymeric resin to provide mechanical protection and minimize Fresnel's losses, said coating having favorable transmission characteristics in the wavelength range of the light source assembly.

19. The assembly of claim 18, wherein said substrate is fabricated from one of a ceramic resin and a plastic resin.

20. The assembly of claim 19, wherein said coating has a refractive index of:

$$\sqrt{n_{LED}*n_o}$$

where:
$n_{LED}$=LED index of refraction; and
$n_0$=substrate material index of refraction.

21. The assembly of claim 1, further comprises at least one sensor for monitoring and controlling any of skin temperature and surface hydration at said measurement site.

22. The assembly of claim 1, wherein said assembly is incorporated into an instrument for noninvasive glucose determination.

23. An instrument for non-invasive blood analyte determination comprising:
a light source assembly for non-invasive optical sampling comprising:
a plurality of LED's, wherein at least one of said plurality of LED's emits at a wavelength region different from and overlapping with that of at least another of said plurality of LED's;
a LED substrate; said substrate providing mechanical support for said LED's, so that said LED's and said substrate form a LED/substrate subassembly;
means for controlling light intensity profile;
means for electrically connecting said LED's;
means for shaping light beams emitted from said LED's;
means for coupling said signal to a sample interface;
means for collecting light emitted from said sample:
wherein said LED's are combined to provide a wide band signal coupled to a tissue measurement site and wherein light emitted from a sample is collected; and
wherein said means for shaping light beams emitted from said LED's comprises a plurality of parabolic reflectors, wherein each reflector is mounted within a well on an anterior face of said substrate, and wherein each of said LED's is fixedly attached within a corresponding reflector, so that divergence between light beams is minimized;
an optical module, for any of dispersing, focusing and detecting said emitted light;

a LED driver for powering said LED's;

processor means for executing a prediction algorithm; and display means for outputting said analyte determination.

24. The instrument of claim 23, wherein said substrate has a posterior face and sides.

25. The instrument of claim 23, wherein said LED/substrate sub-assembly is coated with one of optical epoxy and a polymeric resin to provide mechanical protection and minimize Fresnel's losses, said coating having favorable transmission characteristics in the wavelength range of the light source assembly.

26. The instrument of claim 25, wherein said means for electrically connecting said LED's comprises bonding wires for interconnecting said LED's.

27. The instrument of claim 26, where said means for electrically connecting said LED's further comprises a metallization pattern on the anterior face and sides of said substrate, said metallization pattern forming electrical contacts for contacting said bonding wires.

28. The instrument of claim 27, wherein said means for electrically connecting said LED's further comprises a metallization pattern on a printed circuit board (PCB), said PCB having an anterior face and a posterior face, said anterior face of said PCB defining a self-aligning indent adapted to receive said LED/substrate sub-assembly, said metallization providing electrical contacts that contact said electrical contacts on said substrate when said substrate is seated in said indent; wherein said PBC that in turn contacts said LED driver, so that said LED's are electrically connected to said LED driver;

wherein said LED's are connected to said LED driver either individually or in groups.

29. The instruments of claim 28, wherein said PCB defines an aperture, so that said substrate conduit and said PCB aperture align when said LED/substrate sub-assembly is seated in said PCB.

30. The instrument of claim 29, wherein said temperature regulating elements comprises a thermo-electric cooler, having a cold side and hot side, that fits through said aperture to be recieved by said posterior well so that said cold side is in contact with said posterior face of said substrate; and a heat sink, said heat sink in contact with said hot side of said cooler, wherein said thermo-electric cooler and said heat sink together comprise a thermoelectric cooler-heat sink subassembly.

31. The instrument of claim 30, further comprising a support ferrule, wherein said collection fiber passes through said PCB aperture and said thermoelectric cooler-heat sink subassembly to be recieved by said ferrule at the posterior face of said PCB.

32. The instrument of claim 26, wherein said LED driver comprises:

a module for powering said LED's, so that said individual LED's and said groups of LED's are:

serially addressable, one LED or group of LED's at a time;

simultaneously addressable, all LED's or groups of LED's at a time; and wherein selected groups or selected LED's are flexibly sequenceable according to one or more stored, pre-programmed sequences.

33. The instrument of claim 32, wherein said module produces pulses of approximately 100–400 nanoseconds, with programmable high peak current of up to 10 amps, and wherein said module drives LED's or groups of LED's in continous wave mode at current levels of approximately 100–500 mA, and wherein said LED module drives said LED's or groups of LED's under either of AC or DC conditions.

34. The instrument of claim 23, wherein said means for coupling said signal to a sample interface comprises a mixer, said mixer comprising a large diameter fiber optic having a hollow center and having a high index of refraction, so that wavelength content and intensity of light beams emanating from said LED/substrate sub-assembly are throughly mixed without introducing additional light loss.

35. The instrument of claim 34, wherein said mixer is fixedly mounted on said anterior face of said substrate.

36. The instrument of claim 35, wherein said means for collecting light emitted from said sample comprises a collection fiber, said collection fiber comprising a second fiber optic threaded through said hollow center and passing through a conduit from said anterior face of said substrate to a well in said posterior face of said substrate, said well being dimensioned to receive a temperature regulation element.

37. The instrument of claim 36, wherein said optical module comprises:

a miniature spectrum analyzer having entry and output slits;

a linear detector array module, said spectrometer and said dector array module fixedly attached to each other such that said output slit and a face of said detector array module are facing.

38. The instrument of claim 37, wherein width of said entry slit equals width of an individual pixel in a linear detector array within said linear detector array assembly.

39. The instrument of claim 38, wherein said spectrum analyzer comprises:

a mirror, wherein a light beam emmitted from said collection fiber and projected through said entry slit is folded by said mirror;

a concave holographic grating, wherein said folded light beam is projected from said mirror and dispersed and focused by said grating;

wherein a flat field section of said spectrum is projected toward said array through said output slit.

40. The instrument of claim 37, wherein said linear detector array comprises a linear photodiode array, each photodiode comprising a detection element and an associated multiplexer element, each photodiode representing a pixel, wherein said photodiodes each simultaneously record a one pixel portion of said projected spectrum, so that the entire spectrum is recorded, and wherein said portions of said recorded spectrum are converted into a voltage by said detection elements.

41. The instrument of claim 40, wherein said multiplexing elements read signals output from each of said detection elements in a serial fashion.

42. the instrument of claim 41, wherein said linear detector array module further comprises a signal conditioning circuit, wherein said multiplexing elements transfer said signals to said conditioning circuit of conditioning though any of:

buffering;

impedance matching;

frequency smoothing; and level-shifting.

43. The instrument of claim 42, wherein said linear detector array assembly further comprises an analog-to-digital conversion circuit (ADC), wherein said signal conditioning circuit transfers said conditioned signal to said ADC;

wherein said ADC converts said conditoned signal to digital values and transfers said digital values to said processor means.

44. The instrument of claim 43, wherin said processor means comprises a high speed digital electronics module, said module including:

a digital signal processor; and at least one memory;

wherein said module receives said digital values form said optical module and processes said digital values according to said prediction algorithm to arrive at an estimate of target analyte concentration.

45. The instrument of claim 44, wherein said memory comprises non-volatile memory, and wherein said algorithm is stored in said non-volatile memory.

46. The instrument of claim 44, wherein said memory comprises volatile memory, and wherein said digital values are stored in said volatile memory.

47. The instrument of claim 23, wherein said display means comprises a high-resolution LCD.

48. The instrument of claim 23, further comprising a power supply, said power supply comprising a nickel-metal-hydride battery.

49. The instrument of claim 23, further comprising a control means, said control means comprising one of keypad and a speech recognition module.

50. The instrument of claim 22, wherein said sample interface comprises a fiber optic probe.

51. The instrument of claim 23, wherein said prediction algorithm estimates concentration of a target analyte based on spectroscopic analysis of light emitted from a sampling site.

52. The instrument of claim 23, wherein said analyte comprises glucose.

53. The instrument of claim 22, further comprising at least one sensor for monitoring and controlling any of skin temperature and surface hydration at said measurement site.

* * * * *

UNITED STATES PATENT AND TRADEMARK OFFICE
CERTIFICATE OF CORRECTION

PATENT NO. : 6,816,241 B2
DATED : November 9, 2004
INVENTOR(S) : Grubisic It is certified that error appears in the above-identified patent and that said Letters Patent is hereby corrected as shown below:

<u>Title page,</u>
Item [75], Inventors, replace "Dragan Grubisic" with -- Dragan Grubisic, Kevin Hazen, Timothy L. Ruchti, and George Acosta --

Signed and Sealed this

Tenth Day of May, 2005

JON W. DUDAS
*Director of the United States Patent and Trademark Office*